United States Patent [19]

Schwadrohn

[11] Patent Number: 5,506,220
[45] Date of Patent: Apr. 9, 1996

US005506220A

[54] ANTI-GLAUCOMATOUS PHARMACEUTICAL COMPOSITION AND THE PROCESS FOR OBTAINING THEM

[75] Inventor: Gérard Schwadrohn, Nice, France

[73] Assignee: Laboratoire Theramex SA, Monaco

[21] Appl. No.: 170,179

[22] PCT Filed: Jun. 18, 1992

[86] PCT No.: PCT/FR92/00549

§ 371 Date: May 25, 1994

§ 102(e) Date: May 25, 1994

[87] PCT Pub. No.: WO92/22300

PCT Pub. Date: Dec. 23, 1992

[30] Foreign Application Priority Data

Jun. 18, 1991 [FR] France ................... 91 07412
Jul. 17, 1991 [FR] France ................... 91 09015
Jul. 17, 1991 [FR] France ................... 91 09016
Jul. 17, 1991 [FR] France ................... 91 09017
Aug. 9, 1991 [FR] France ................... 91 10160

[51] Int. Cl.$^6$ ................. A61K 31/58; A61K 31/56
[52] U.S. Cl. ................. 514/172; 514/178; 514/181
[58] Field of Search ................. 514/172, 181, 514/178

[56] References Cited

U.S. PATENT DOCUMENTS 4,383,992  5/1983  Lipari ........................... 424/238

*Primary Examiner*—Allen J. Robinson
*Assistant Examiner*—Mary C. Cebulak
*Attorney, Agent, or Firm*—Bierman and Muserlian

[57] ABSTRACT

The invention relates to the domain of medicinal chemistry. It concerns more particularly that of the preparation of pharmaceutical compositions for ocular use.

A subject of the invention is pharmaceutical compositions for ocular use characterized in that they contain at least one selected compound of steroidal structure in combination with or admixed with a pharmaceutically-acceptable, inert carrier or vehicle.

The compositions according to the invention are intended to the treatment of glaucoma.

12 Claims, No Drawings

ANTI-GLAUCOMATOUS PHARMACEUTICAL COMPOSITION AND THE PROCESS FOR OBTAINING THEM

This application has been filed under 37 CFR 371 from patent application PCT/FR92/00549 which was filed on Jun. 18, 1992.

The invention relates to the domaine of medicinal chemistry and in particular to the pharmacotechnology domain.

A specific subject of the invention is pharmaceutical compositions for ocular use, characterised in that they contain as active ingredient, at least one compound of steroidal structure selected from the group consisting of

A-19-NOR PREGNA 4,6-DIENES OF GENERAL FORMULA I

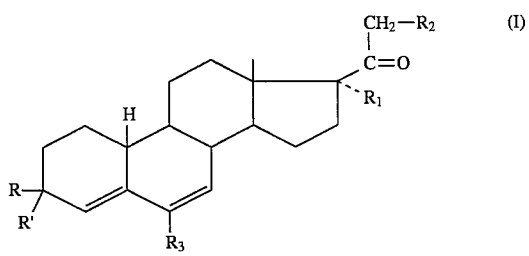

in which
  R1 represents a hydroxy, an alkoxy and an acyloxy radical
  R2 represents hydrogen or a lower alkyl radical
  R and R' together form a keto, hydroxyimino, alkoxyimino or acyloxyimino group
  or separately, when R=H, R' is a hydroxy, an alkoxy or an acyloxy group
  and R3 represents a lower alkyl radical having 1 to 3 carbon atoms

R-19-NOR 4,6-DIENES OF GENERAL FORMULA II

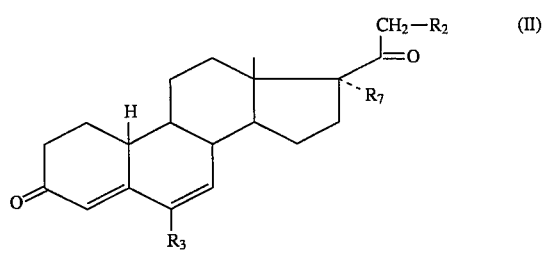

in which
  R2 represents a hydrogen atom or linear or branched chain an alkyl radical having 1 to 6 carbon atoms, R7 represents a lower alkyl radical, identical to or different from R2, having 1 to 6 carbon atoms, as a linear or branched chain
  and R3 is defined as previously

C-COMPOUNDS OF 19-NOR PREGNENIC STRUCTURE, OF GENERAL FORMULA III

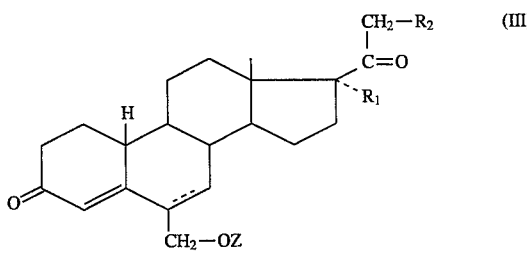

in which
  R1 represents a hydroxy, an alkoxy, an acyloxy or an alkyl radical having 1 to 4 atoms
  R2 represents an hydrogen or a lower alkyl radical as a linear or branched chain having 1 to 4 carbon atoms
  Z represents hydrogen, an alkyl radical or an acyl radical
  and the dotted line represents an optional carbon-carbon double bond

D-19-NOR PREGNENIC DERIVATIVES OF GENERAL FORMULA IV

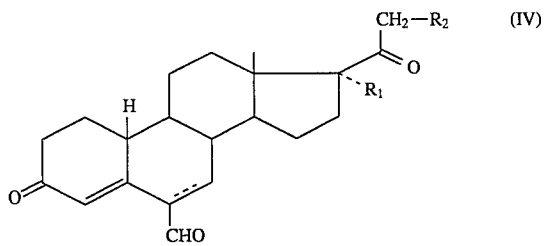

in which
  R1 represents a hydroxy, an alkoxy, an acyloxy or an alkyl radical having 1 to 4 carbon atoms
  R2 represents a hydrogen or a lower alkyl radical, as a linear or branched chain, having 1 to 4 carbon atoms
  and the dotted line symbolizes an optional carbon-carbon double bond

E-6-HALOMETHYL 19-NOR PREGNENIC DERIVATIVES OF GENERAL FORMULA V

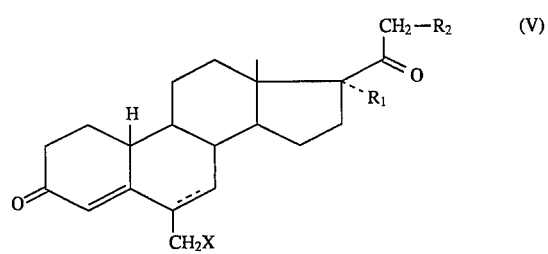

in which
  X represents a halogen atom
  R1 and R2 are defined as previously
  and the dotted line symbolizes an optional carbon-carbon double bond

F-COMPOUNDS OF 19-NOR ANDROSTENIC STRUCTURE CORRESPONDING TO GENERAL FORMULA VI

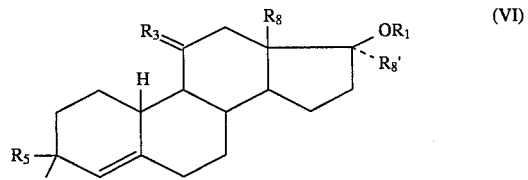

in which
  R1 represents a hydrogen, a lower alkyl or an acyl radical derived from an organic carboxylic acid having 1 to 10 carbon atoms
  R' represents a hydrogen or a lower alkynyl
  R represents a methyl or ethyl
  R5 represents two hydrogen or the group =O, =N—OH
  or

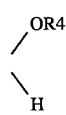

in which R4 represents a hydrogen or the acyl residue of an organic carboxylic acid
and R3 represents two hydrogens or =CH2

G-PREGNADIENES OF GENERAL FORMULA VII

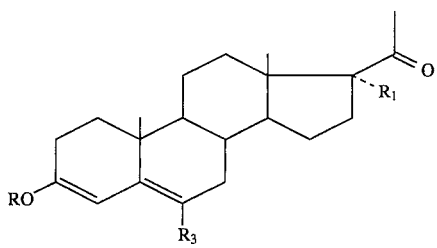

in which

R$_9$ represents a lower alkyl or lower cycloalkyl radical
R1 and R3 are defined as previously

H-PREGNENIC DERIVATIVES OF GENERAL FORMULA VIII

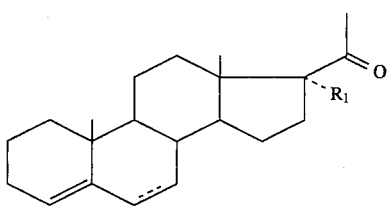

in which the dotted line represents an optional double bond and R1 is defined as previously

I-3,2,0-DIOXO DELTA 4-PREGNENIC COMPOUNDS CORRESPONDING TO GENERAL FORMULA IX

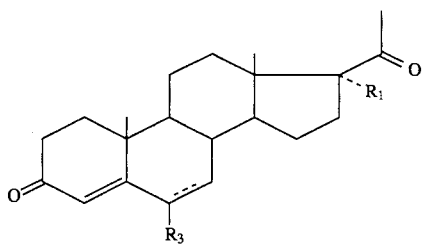

in which

R1 represents a free, etherified or esterified hydroxyl radical or a lower alkyl radical R3 represents hydrogen or a lower alkyl radical having 1 to 4 carbon atoms and the dotted line symbolizes 2 hydrogens or a carbon-carbon double bond

J-11,18-EPOXYANDROSTENIC COMPOUNDS OF GENERAL FORMULA X

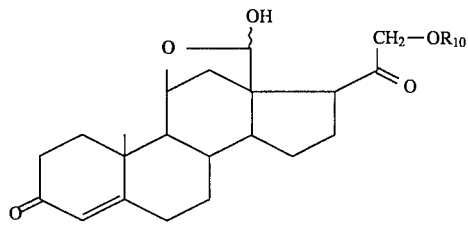

in which, the wavy line symbolizes an alpha or beta orientation and R$_{10}$ represents a hydrogen or an acyl radical derived from an organic carboxylic acid having 1 to 10 carbon atoms

K-CORTICOSTEROIDS OF GENERAL FORMULA XI

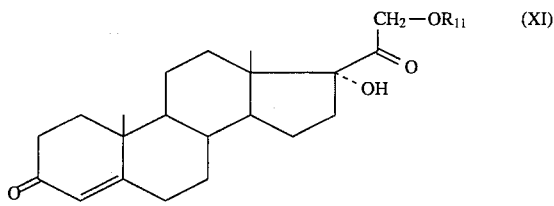

in which

R$^{11}$ represents hydrogen or an acyl radical derived from an organic carboxylic acid having 1 to 10 carbon atoms and L-ANDROSTENIC COMPOUNDS OF GENERAL FORMULA XII

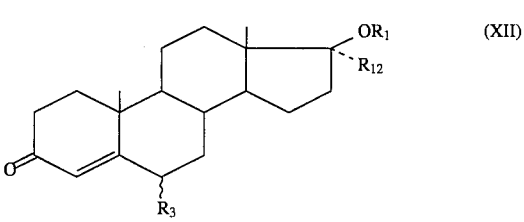

in which

R1 represents a hydrogen, a lower alkyl radical, a methoxy alkyl, an acyl residue derived from an organic carboxylic acid or an alkyl carbonic acid R$_{12}$ represents a hydrogen or an optionally substituted alkyl radical R3 represents a hydrogen, a halogen or a lower alkyl and the wary line symbolizes an alpha or beta orientation combined or mixed with a pharmaceutically-acceptable, inert excipient or vehicle, intended for use by ocular route.

To this end, the pharmaceutical compositions are, according to the invention, preferably presented in solid form for extemporaneous dissolution, semi-solid or liquid form, the compounds of formula I, formula II, formula III, formula IV, formula V, formula VI, formula VII, formula IX, formula X, formula XI or formula XII being in the form of a suspension or dissolved in solution, distributed in flasks, tubes or single-dose systems.

Among the compounds of general formula I, there can be mentioned quite particularly, the derivatives of 17alpha-hydroxy 19-nor pregna 4,6-diene, 3,20-dione of general formula Ia

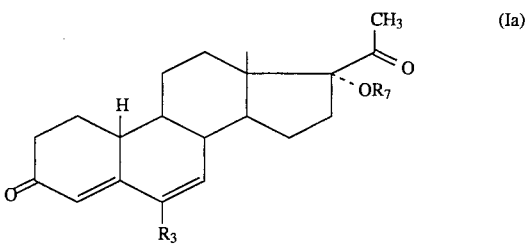

in which

R7 represents a hydrogen atom, an acyl radical having 1 to 8 carbon atoms and R3 is a methyl or propyl radical Among the compounds of general formula III, there can be mentioned quite especially:

a) the derivatives of 17alpha-hydroxy 19-nor pregna 4,6-diene 3,20-dione of general formula IIIa

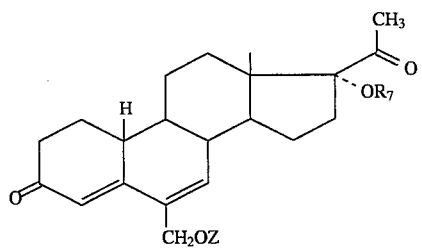

in which

R7 represents a hydrogen atom, an alkyl radical having 1 to 8 carbon atoms, a 2-tetrahydropyranyl radical or an acyl radical derived from a saturated or unsaturated, aliphatic carboxylic acid, having 1 to 10 carbon atoms, optionally substituted by an aryl or cycloalkyl radical Z is defined as previously These products are described in the French Patent Application n° 91.09097 filed in the name of the applicant on Jul. 18, 1991.

b) the derivatives of 17-alpha-hydroxy 21-methyl 19-nor pregna-4,6 diene 3,20-diones of general formula IIIb

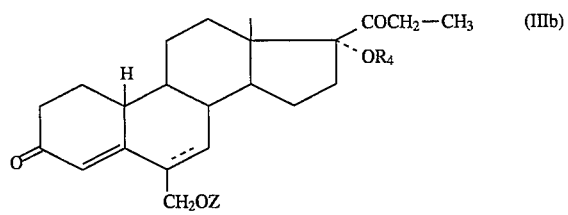

in which

R4 represents a hydrogen atom, a lower alkyl radical, a methoxymethyl radical, a 2-tetrahydropyranyl radical or an acyl radical of an organic carboxylic acid having from 1 to 10 carbon atoms Z is defined as previously These compounds are enclosed in the general formula of the french patent application n° 91,09097 filed on Jul. 18, 1991 in the name of the applicant.

c) the derivatives of 17alpha and 21-alkyl of 19-nor pregna-4,6 diene 3,20-diones of general formula IIIc

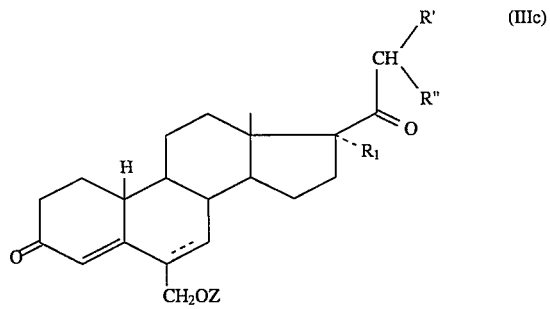

in which

R' and R" each represent a hydrogen atom or an alkyl radical having 1 to 3 carbon atoms, as a linear or branched chain R1 represents a lower alkyl radical, identical to or different from R' and R", having from 1 to 3 carbon atoms, as a linear or branched chain Z is defined as previously These compounds are enclosed in the general formula of the french patent application n° 91.09097 filed on Jul. 18, 1991 in the name of the applicant d) the 19-nor pregna 4-ene derivatives of general formula IIId

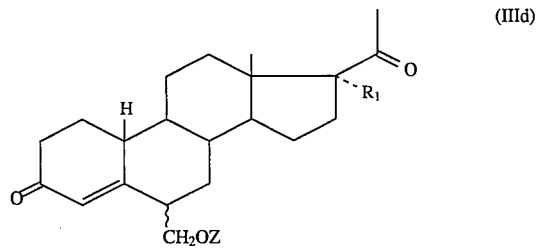

in which

R1 is an alkyl radical, a hydroxy, an alkoxy, an acyloxy and the wavy line indicates an alpha or beta orientation and Z is defined as previously These compounds are enclosed in the french patent application n° 91.09097 filed on Jul. 18, 1991 in the name of the applicant

• Among the compounds of general formula IX, there can be mentioned in particular:
17alpha-hydroxy progesterone
17alpha-acetoxy progesterone
17alpha-methoxy progesterone
6alpha-methyl 17alpha-acetoxy progesterone
6-methyl 17alpha-acetoxy 3,2-dioxo pregna 4,6-diene
6alpha, 17alpha-dimethyl 3,20-dioxo pregna-4-ene

• Among the compounds of general formula X, there can be mentioned in particular the isoaldosterone of formula

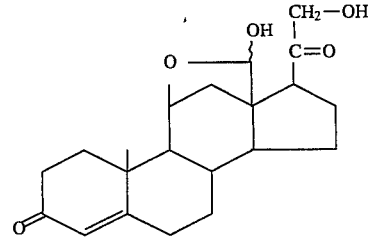

as well as its aliphatic or aromatic esters.

• Among the compound of general formula XI, there can be mentioned in particular Cortexolone

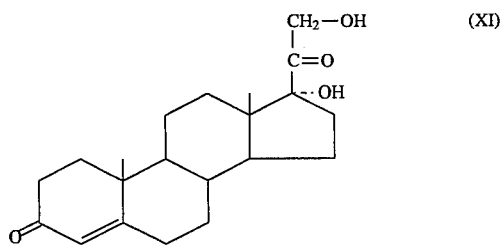

and the aliphatic or aromatic mono- or diesters thereof

• Among the compounds of general formula V, there can be mentioned quite particularly:
3,20-dioxo 17alpha-acetoxy 6-chloromethyl 19-nor pregna 4,6-dien of formula Va

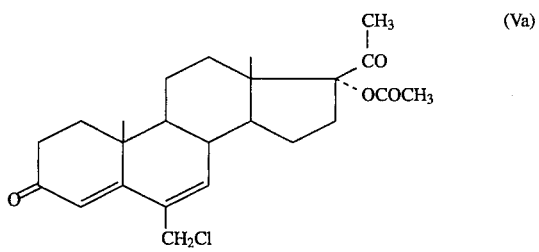

and 3,20-dioxo 17alpha-acetoxy 6-fluoromethyl 19-nor pregna 4,6-diene of formula Vb

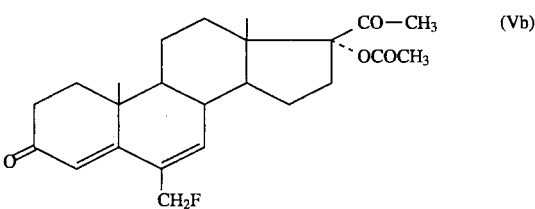

• Among the compounds of general formula VI, there can be mentioned in particular:
19-nor testosterone
17-alpha-ethynyl 19-nor testosterone
3beta, 17beta-diacetoxy 17alpha-ethynyl 19-nor delta4-androstene
3-oximido 17alpha-ethynyl 19-nor testosterone
3-oxo 17alpha-ethynyl 17beta-hydroxy 13-ethyl gona 4-ene
11-methylene 17alpha-ethynyl 17beta-hydroxy 13beta-ethyl gona 4-ene.

e) among the compounds of general formula XII, there can be mentioned more particularly:

a) 3-oxo androsta 4-enes of general formula XIIa

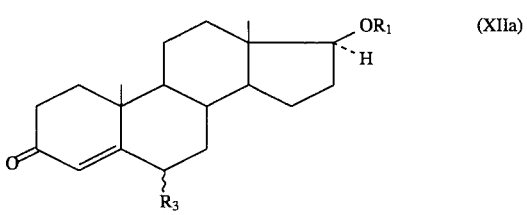

in which
R1 represents a hydrogen, an optionally substituted alkyl radical or an acyl radical derived from an organic carboxylic acid or an alkyl carbonic acid having from 1 to 8 carbon atoms
and R3 is defined as previously b) 3-oxo 17beta-alkyl androsta 4-enes of general formula XIIb

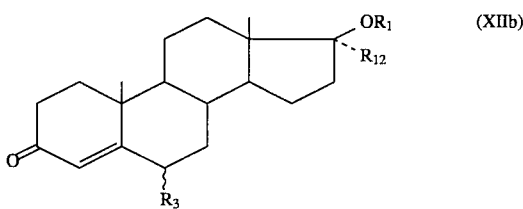

in which
R1 represents a hydrogen or an acyl radical defined as above
$R_{12}$ is a lower alkyl radical optionally substituted by a halogen or an acyl R3 is hydrogen or a lower alkyl The thus-obtained preparations have added to them, if necessary, mineral salts or organic derivatives in order to achieve isotonicity with lacrymal secretions, preservatives or stabilizers and/or anti-oxidants. As stabilizers, there can be mentioned more particularly chelating agents such as ethylene diaminotetraacetic acid and its salts. As anti-oxidants, there can be mentioned ascorbic acid, alkali metal metabisulphites, alkali metal hypophosphites, sodium salicylate, sodium gentisate or isopropyl gallate.

In what precedes and except for indication to the contrary, a lower alkyl radical possesses from 1 to 6 carbon atoms such as a methyl, ethyl, isopropyl, tertbutyl, isobutyl, n-pentyl, neopentyl or n-hexyl radical.

A halogen is a fluorine or chlorine atom.

An acyl residue of an organic carboxylic acid contains 1 to 10 atoms in t he hydrocarbon part such as for example an acetyl, a propionyl, a hexanoyl, a benzoyl, a dichloroacetyl, a vanilloyl, an isovanilloyl, a trimethoxy benzoyl, a naphthoyl (alpha or beta), a furoyl, a nicotinoyl or a thenoyl.

An alkyl residue of an alkyl carbonic acid contains 1 to 8 carbon atoms in the alkyl chain, such as for example a (cycloalkyl)methyl carbonic radical or a (cycloalkyl)propyl carbonic radical.

The compositions according to the invention relates to the treatment of intraocular hypertension and glaucomatous diseases. They contain from 0.05 to 1% of steroidal active ingredient. They are prepared by putting an active ingredient in solution or in suspension in a suitable aqueous solvent.

It is already known that three types of glaucoma exist:
1. primary glaucomas which represent 86% of all glaucomas. Two types can be distinguished from this category which are quite particularly important:
   open-angle glaucoma (OAG)
   closed-angle glaucoma (CAG)
2. secondary glaucomas
3. congenital glaucomas The clinical signs of these diseases are those of an optical neuropathy with:
lowering of visual acuity
deficiency of the field of vision
alteration of the optical nervous fibers, leading progressively to blindness An intraocular pressure (IOP) of greater than 15 mmHg±2.5 mmHg is observed in the majority of cases.

All of the current treatments aim at normalizing this IOP which is the most immediately quantifiable sign and which guarantees the effectiveness of the treatment.

Current local treatments have pharmacological effects similar to those of hormones of the autonomous nervous system, whether sympathomimetic or para-sympathomimetic (adrenaline, epinephrine, pilocarpine . . .).

The discovery over the last ten years of the action of beta-blocking products has also reinforced the importance of the sympatho- and para-sympathomimetic systems tat the ocular level.

The general treatments used (per os or as a perfusion) aim, like the local treatments, at decreasing the formation of the aqueous humor (an exception is made for pilocarpine).

All these treatments have inconveniences which make regular medical supervision necessary. The use of these products presents numerous and significant contraindications:
• beta-blockers: bronchial asthma, cardio-vascular insufficiency, etc. . .

anti-glaucomatous sympathomimeties (iridocyclitis) and numerous undesirable effects (corneo-conjunctival reactions, hydriasis or miosis of the iris, ocular dryness, modification of the field of vision, cardiovascular effects, general respiratory effects, dermatological effects . . .) which vary according to the nature of the product.

The pharmaceutical compositions according to the invention aim at improving this situation. They have at least an equal effectiveness, but above all their tolerance and their innocuity at the doses tested are significantly better. Moreover, they address both open-angle and closed-angle glaucomas and show practically none of the undesirable side effects and the above mentioned contra-indications.

Previous studies had already attempted to demonstrate the regulatory role of progesterone on the IOP of a normal eye. Progesterone and even the hormone of the corpus luteum had already been used. It was noted that these products lowered the intraocular pressure in an objective but above all temporily way, which effect the authors attributed to the diuretic action of progrestative agents, the parasympathicotropic action of lutein which diminishes mydriasis due to atropine in rats and finally to the antagonist effect of the hypotensive action on the eye, of folliculin (cf. Ärztlich. Wochenschrift 5 (1950) 34). More recently, TZU LUNG CHIANG, (Prostaglandins 4, 3 (1973) 415), has shown that progesterone inhibited the hypertensive response of the eye to the intravenous perfusion of PGA2. However, in order to bring about a significant although short-lasting effect, the doses of progesterone administered were considerable (25 mg/kg). The same author (Europ. J. of Pharmacology 22 (1973) 304) confirmed that progesterone antagonized the increase of intraocular pressure.

The effects of progesterone appear to result from a synergy with the effect of epinephrine or ephedrine, administered locally.

The conclusions of the authors are that the effectiveness of the treatment of progesterone against intraocular hypertension, in response to prostaglandins, was limited. A very high dose of progesterone administered frequently was necessary. According to these same authors, the action of progesterone would result in a synergy with circulating catecholamines.

Moreover, PGE, administered by perfusion through a vein, completely inhibits the increase in the level of protein production in the aqueous humor.

In addition, this ocular action of the progestomimetic products seems to be independent of the known properties of progesterone and above all have no correlation with a progestomimetic effect. This is why the effectiveness of the pharmaceutical compositions according to the invention, is not relative to the known level of affinity of the active ingredient for the progesterone receptor or to the level of progesterone activity.

This action seems to be exerted on the structures responsible for the evacuation of the aqueous humor. It was therefore interesting to discover and experiment with similar steroid products to determine those which would be the most effective and in particular androstane derivatives which is as though lacked progesterone action.

The useful dosages range from 1 to 5 drops per day in each eye of a solution or suspension containing from 0.05 to 1% of an active ingredient of general formula I to XII. Preferably, the solutions or suspensions contain 0.1 to 0.5% of active ingredient of general formulae I to XII.

Two experimental models are used to test the compounds according to the invention:

- experimental glaucoma model in a rabbit by injection of a 5% glucose solution: this model, described by BONOMI et Coll, shows that the injection of 5% glucose in a rabbit causes an increase in intraocular pressure of 8 mmHg in 5 to 10 mn, then a return to normal in about 40 minutes. The mechanism of this modification of the IOP is explained by the reduction of osmolarity of the blood by hemodilution as well as a decrease in the ease of flow of the aqueous humor by hydration of the trabeculum cells.
- experimental glaucoma model by injection of alpha-chymotrypsin: the glaucoma is caused one month before the tests are carried out by injection, in the posterior chamber of an eye, of a proteolytic enzyme, alpha-chymotrypsin. This causes lysis of the lens zonule, a dislocation of the lens in the posterior chamber and a hypertension by mechanical obstruction of the iridocorneal angle.

On these models, the compounds according to the invention, at a concentration of 0.1 to 0.5%, cause a rapid and significant decrease, linked to the concentration, of the intraocular pressure.

Quite particularly:

17alpha-methyl 17beta-hydroxy 3-oxo androsta 4ene and its esters 6-pivaloyloxymethyl 3,20-dioxo 17alpha-acetoxy 19-nor pregna 4,6-diene cortexolone and its esters 17alpha-hydroxy progesterone and 3,20-dioxo 6-hydroxymethyl 17alpha-acetoxy 19-nor pregna 4,6-diene bring about a significant drop in intraocular pressure in the animal which has been made hypertensive and the decreases obtained are highly significant from a statistical point of view (p<0.01).

I claim:

1. A composition for treating glaucoma comprising an amount of a compound of the formula

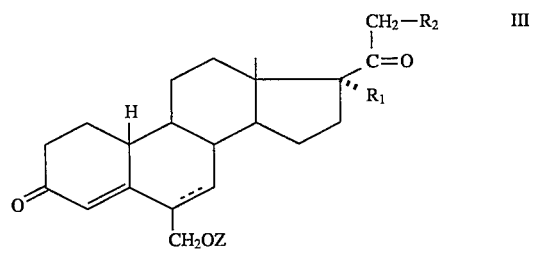

wherein $R_1$ is selected from the group consisting of —OH, alkyl and alkoxy of 1 to 4 carbon atoms and acyloxy of an organic carboxylic acid of 1 to 10 carbon atoms, $R_2$ is hydrogen or alkyl of 1 to 4 carbon atom, Z is selected from the group consisting of hydrogen, alkyl of 1 to 4 carbon atoms and acyl of an organic carboxylic acid of 1 to 4 carbon atoms and the dotted line is an optional double bond sufficient to treat glaucoma and a pharmaceutically acceptable inert vehicle.

2. A composition according to claim 1 in which the active ingredient is a derivative of 17alpha-hydroxy 3,20-dioxo 19-nor pregna 4,6-diene of the formula

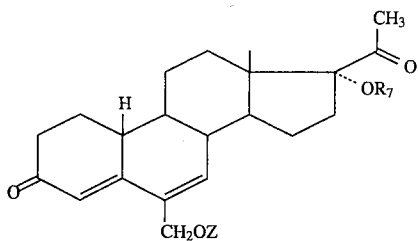

in which Z is defined as previously and $R_7$ is alkyl of 1 to 4 carbon atoms.

3. A composition according to claim 1 in which the active ingredient is a derivative of 17alpha-hydroxy 3,30-dioxo 21-methyl 19-nor pregna 4,6-diene of the formula

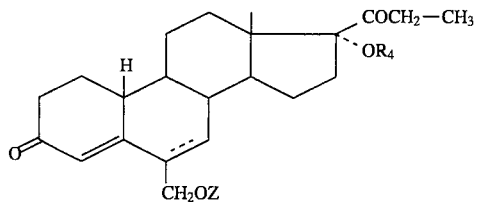

in which Z is defined as previously and $R_4$ is hydrogen of acyl of an organic carboxylic acid of 1 to 10 carbon atoms.

4. A composition according to claim 1 in which the active ingredient is an alkylated derivative of 3,20-dioxo 19-nor pregna 4,6-diene of the formula

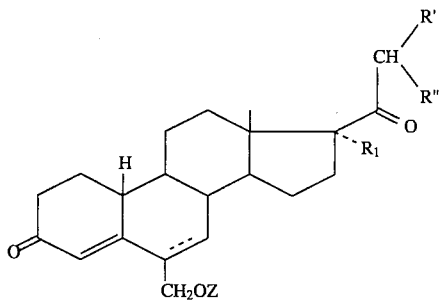

in which Z and R1 are defined as above and R' and R" are individually hydrogen or alkyl of 1 to 4 carbon atoms.

5. A composition according to claim 1 in which the active ingredient is a 19-nor pregna 4-ene derivative of the formula

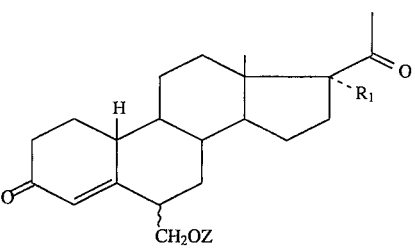

in which Z and R1 are defined as previously.

6. A pharmaceutical composition according to claims 1 and 3 in which the active ingredient is 6-(pivaloyloxy methyl) 17alpha-hydroxy 3,20-dioxo 19-nor pregna 4,6-diene.

7. A pharmaceutical composition according to claim 1 in which the active ingredient is 17alpha-acetoxy 6-methyl 3,20-dioxo 19-nor pregna 4,6-diene.

8. A pharmaceutical composition according to claim 1 to which a stabilizer is added.

9. A pharmaceutical composition according to claim 1 to which an antioxidant is added.

10. A pharmaceutical composition according to claim 1 in which the content of active ingredient ranges from 0.05 to 1%.

11. A method of treating intraocular hypertension in warm-blooded animals comprising administering to warm-blooded animals in interocular hypertensive effective amount of a compound of the formula

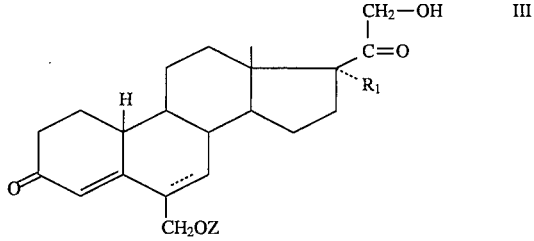

wherein $R_1$ is selected from the group consisting of —OH, alkyl, and alkoxy of 1 to 4 carbon atoms and acyloxy of an organic carboxylic acid of 1 to 4 carbon atoms, Z is selected from the group consisting of hydrogen, alkyl of 1 to 4 carbon atoms and acyl of an organic carboxylic acid of 1 to 4 carbon atoms and the dotted line is an optional double bond.

12. The method of claim 11 wherein the active compound is 6-hydroxymethyl-17α-acetoxy-19-nor-$\Delta^{4,6}$-pregnadiene-3,20-dione.

* * * * *